United States Patent [19]

Schneider

[11] 3,962,248

[45] June 8, 1976

[54] PROCESS FOR MAKING 11-PIPERAZINO-DIAZEPINES, OXAZEPINES, THIAZEPINES AND AZEPINES

[75] Inventor: Josef Schneider, Minusio, Switzerland

[73] Assignee: Sandoz, Inc., Hanover, N.J.

[22] Filed: Feb. 26, 1975

[21] Appl. No.: 553,142

Related U.S. Application Data

[63] Continuation of Ser. No. 346,343, March 29, 1973, abandoned.

[30] Foreign Application Priority Data

Apr. 4, 1972   Switzerland.......................... 4898/72
Apr. 4, 1972   Switzerland.......................... 4901/72

[52] U.S. Cl............................ 260/268 TR; 424/250
[51] Int. Cl.² .............. C07D 403/04; C07D 413/04; C07D 417/04
[58] Field of Search.............................. 260/268 TR

[56] References Cited
OTHER PUBLICATIONS

White et al., J. Org. Chem., vol. 32, pp. 213–214, (1967).
Weingarten et al., J. Org. Chem., vol. 32, pp. 3246–3249, (1967).
Fryer et al., J. Organic Chemistry, vol. 34, pp. 1143–1145, (1969).

*Primary Examiner*—Alton D. Rollins
*Assistant Examiner*—Jose Tovar
*Attorney, Agent, or Firm*—Gerald D. Sharkin; Robert S. Honor; Thomas O. McGovern

[57]  ABSTRACT

This invention concerns a novel process for the preparation of 6-piperazinyl derivatives of morphantridine and corresponding ring-substituted and hetero analogues thereof, comprising reacting a compound of the formula:

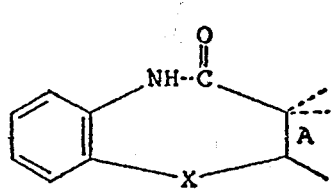

wherein A is benzene or thiophene, and X is $-CH_2-$ or a hetero atom or group, with a complex comprising titanium, zirconium, hafnium or vanadium and a corresponding piperazinyl derivative.

The end products are in general known and useful as neuroleptics.

8 Claims, No Drawings

PROCESS FOR MAKING 11-PIPERAZINO-DIAZEPINES, OXAZEPINES, THIAZEPINES AND AZEPINES

This is a continuation of application Ser. No. 346,343 filed Mar. 29, 1973, now abandoned.

IMPROVEMENTS IN OR RELATING TO ORGANIC COMPOUNDS

The present invention relates to a new process for the production of compounds of formula I,

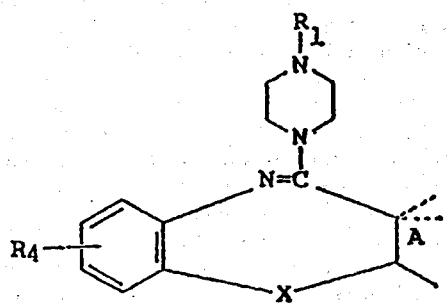

wherein
$R_1$ is hydrogen, alkoxyalkyl of 2 to 6 carbon atoms in the aggregate thereof, alkyl of 1 to 4 carbon atoms, hydroxyalkyl of 1 to 4 carbon atoms, or acyloxyalkyl of 3 to 22 carbon atoms in the aggregate thereof, $R_4$ is hydrogen, alkyl, alkoxy or alkylthio, wherein the alkyl groups have 1 to 4 carbon atoms, halogen, or trifluoromethyl, and A signifies the structure

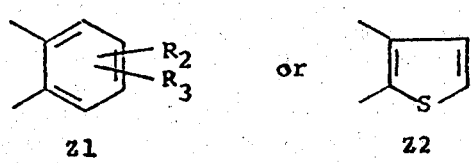

a. when A denotes Z1, X is a —CH$_2$—, —O—, —S—, —NH or —N—alkyl group wherein the alkyl group has 1 to 3 carbon atoms, $R_2$ is hydrogen, alkyl, dialkylamino-sulphonyl, alkylsulphonyl, wherein the alkyl groups have 1 to 4 carbon atoms, alkoxy or alkylthio of 1 to 4 carbon atoms, halogen, nitro, trifluoromethylsulphonyl, trifluoromethoxy, trifluoromethylthio, acetyl, cyano or trifluoromethyl, and $R_3$ is hydrogen, halogen or alkyl of 1 to 4 carbon atoms, or b. when A denotes Z2, X is a —CH$_2$—or —S—group.

In the substituents $R_2$, $R_3$ and $R_4$ halogen preferably denotes chlorine or bromine, especially chlorine. When the hydroxyalkyl group of the substituent $R_1$ is acylated, the acyl group preferably contains at most 18 carbon atoms, especially at most 10 carbon atoms. The acyl group is preferably aliphatic and may be saturated or unsaturated.

In accordance with the invention a compound of formula I may be obtained by a process comprising reacting a compound of formula II,

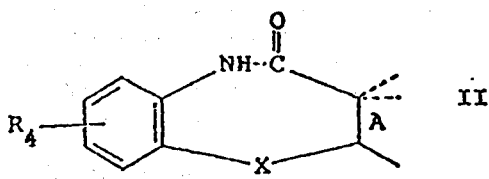

wherein X, A and $R_4$ are as defined above, with a metal-amine complex comprising titanium, zirconium, hafnium or vanadium, and a compound of formula III,

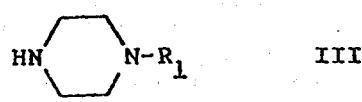

wherein $R_1$ is as defined above.

A resulting compound of formula I wherein $R_1$ is acyloxyalkyl may be saponified to produce a compound of formula I wherein $R_1$ is hydroxyalkyl. A resulting compound of formula I wherein $R_1$ is hydroxyalkyl may be esterified to produce a compound of formula I wherein $R_1$ is acyloxyalkyl.

One preferred method of effecting the process of the invention comprises reacting a compound of formula II with a metal-amine complex in the presence of an acid-binding agent. A tertiary amine, e.g. triethylamine, pyridine, dimethyl-aniline or an excess of a compound of formula III may be used as acid-binding agent. At least one mol, preferably, however, two mols of the acid-binding amino compound should be used, calculated on one mol of metal-amine complex.

The reaction is conveniently effected in an organic solvent, e.g. an aromatic solvent such as toluene, a halogenated aromatic solvent such as chlorobenzene, a halogenated aliphatic solvent such as dichloroethane, or preferably an ether such as anisole. The reaction temperature is not critical within wide limits, and is conveniently from 20°C to 150°C, preferably from 50° to 120°C.

The metal-amine complex used for the reaction of the invention is preferably obtained by reaction of a halide, preferably the tetrachloride or tetrabromide of titanium, zirconium, hafnium or vanadium, with a compound of formula III, conveniently at a mol ratio of 1:4 respectively. The reaction is conveniently effected in the solvent subsequently used for the reaction between a compound of formula II and the metal-amine complex. The metal halide may be used in the form of a soluble (mono- or di) etherate thereof, preferably the anisole dietherate.

It is preferred to use titanium and zirconium and especially titanium.

After the reaction, the compound of formula I may be isolated in conventional manner. The largely insoluble metal compounds present in the reaction mixture may be conveniently removed by conversion into soluble form by the addition of an alcohol, e.g. isopropanol, and by subsequent precipitation by the addition of aqueous ammonia. The compounds of formula I, obtained in accordance with the invention, may be isolated in known manner for example by crystallization from the reaction mixture from which metal compounds have been removed, after concentrating the reaction mixture, and may be subsequently purified in known manner, e.g. by re-crystallization from isopropanol.

When a compound of formula I wherein $R_1$ is hydroxyalkyl is produced, the reaction product may be obtained in colloidal form, since the hydroxyalkyl group can also react with the metal halide with ester formation. In order to avoid the appearance of too much gelatinous material, which could disturb the course of the reaction, it is convenient to effect the reaction in the presence of a large amount of solvent, e.g. chlorobenzene or anisole, preferably in the presence of an excess (10- to 20-fold molar excess) of a tert.amine, e.g. triethylamine.

A compound of formula I wherein $R_1$ is hydroxyalkyl may alternatively be obtained by alkaline saponification of a compound of formula I wherein $R_1$ is an acylated hydroxyalkyl group, e.g. with a dilute sodium hydroxide solution.

The esterification of a compound of formula I wherein $R_1$ is hydroxyalkyl may be effected in known manner, e.g. with a reactive acid derivative, e.g. a halide of a corresponding acid, in a solvent such as chloroform, conveniently in the presence of an acid-binding agent such as triethylamine, at room temperature.

Free base forms of the compounds of formula I produced in accordance with the invention may be converted into their acid addition salt forms in conventional manner and vice versa. Examples of suitable salts are the hydrochlorides, hydrobromides, sulphates, fumarates, maleates and p-toluenesulphonates.

The compounds of formula II, used as starting materials in the process according to the invention, are known or may be produced according to known methods or according to methods described in the Examples hereafter for the production of 10H-thieno[3,2-c][1]benzazepines, or according to methods analogous to any of these methods.

The compounds of formula III, used as starting materials in the process according to the invention are known or may be prepared according to known methods or according to methods described in the Examples hereafter for the production of 1-tert-butylpiperazine, or according to methods analogous to any of these methods.

For example a compound of formula III wherein $R_1$ is acyloxyalkyl may be obtained by reacting N-benzylpiperazine with a halo- alcohol, esterifying the hydroxy group of the N-benzyl-N'-hydroxy-piperazine with a reactive acid derivative, e.g. a halide, especially the chloride of a corresponding acid, and subsequently removing the benzyl group from the resulting compound hydrogenolytically.

Compounds of formula I produced in accordance with the present invention are in general known, and have been described in the literature.

The compounds of formula I are useful because they possess pharmacological activity in animals. In particular the compounds are useful as neuroleptics as indicated by a suppression of locomotor activity in mice on p.o. administration of 0.1 to 5 mg/kg animal body weight of the compounds, in accordance with the method of Caviezel and Baillod, described in Pharm. Acta Helv. 33, 465–484 (1958).

For the above-mentioned use, the dosage to be administered will naturally vary depending on the compound used, the mode of administration and the treatment desired. However, in general, satisfactory results are obtained when administered at a daily dosage of from about 0.01 mg to about 10 mg per kg animal body weight, conveniently given in divided doses 2 to 4 times a day or in sustained release form. For the larger mammals, the total daily dosage is in the range from about 1 to about 500 mg, and dosage forms suitable for oral administration comprise from about 0.25 mg to about 250 mg of the compound admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the maleate, fumarate and tartrate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions may be prepared by conventional techniques to be in the form of, for example, capsules, tablets, suspensions or solutions, for enteral or parenteral administration. Aside from the usual pharmaceutical diluents or carriers, e.g. water, alcohol, talc, stearic acid, natural or hardened oils and waxes, these pharmaceutical compositions may contain suitable preserving, stabilizing, wetting, solubilizing, sweetening, flavouring or colouring agents.

In the general formula I, when A denotes Z1, the substituent $R_2$ is preferably in the 2 or 3 position, the substituent $R_3$ is preferably in the 4 position, and when A denotes Z1 and Z2, the substituent $R_4$ is preferably in the position 7 or 8, i.e. meta or para to the group or atom X.

In the following non-limitative Examples all temperatures are indicated in degrees Centigrade, room temperature is a temperature between 20° and 30°C, unless otherwise indicated.

EXAMPLE 1

8-chloro-11-(4-methyl-1-piperazinyl)-5H-dibenzo[b,e][1,4]diazepine 840 cc of toluene, 90 cc of anisole and 79.2 g of titanium tetrachloride are introduced, at room temperature, in a 2.5 liter sulphonating flask provided with a dropping funnel, reflux condenser and thermometer, whereby a dark brown, clear solution is formed. A mixture of 167 g of N-methyl piperazine and 100 cc of toluene is added thereto while cooling externally with water, whereby the temperature rises to 50°–55° and the amine complex, in finely divided form, forms a beige to dark brown coloured suspension. 102 g of 8-chloro-10,11-dihydro-11-oxo-5H-dibenzo[b,e][1,4]-diazepine and 83 g of N-methyl piperazine are subsequently added, and the reaction mixture is heated to the boil (110°–112°) for 3 hours while stirring. Cooling is then effected to 60°–70°, 125 cc of isopropanol are added, whereby the insoluble titanium compounds formed during the reaction again dissolve. After the addition of 8 g of diatomaceous earth and subsequently 115 cc of concentrated ammonia (about 27%), cooling is effected to about 30° while stirring and the resulting precipitate is filtered off. The filter residue is washed with 2–3 330 cc portions of toluene. The filtrate is subsequently mixed with water, and the organic phase is extracted with dilute, approx. 10% hydrochloric acid. The base is precipitated by the dropwise addition of the hydrochloric acid extract to an excess of dilute ammonia. The precipitate is taken up in ether, the ether solution is washed with water and dried over sodium sulphate. After removal of the ether by evaporation and recrystallization from isopropanol, 8-chloro-11-(4-methyl-1-piperazinyl)-5H-dibenzo-[b,e][1,4]diazepine, having a M.P. of 184°–185°, is obtained.

EXAMPLE 2

6-(4-tert-butyl-1-piperazinyl)-morphantridine 840 cc of toluene, 90 cc of anisole and 93.5 g of zirconium tetrachloride are introduced at room temperature in a 2.5 liter sulphonating flask provided with a dropping funnel, reflux condenser and thermometer, whereby a dark brown, clear solution is formed. A mixture of 248 g of N-tert-butyl piperazine and 100 cc of toluene is added thereto while cooling externally with water, whereby the temperature rises to 50°–55° and the amine complex, in finely divided form, forms a dark brown coloured suspension. 87 g of morphantridin-6-one and 123.5 g of N-tert-butyl piperazine are subsequently added and the reaction mixture is heated to the boil (110°–112°) for 3 hours while stirring. Cooling is then effected to 60°–70°, 125 cc of isopropanol are added, whereby the insoluble zirconium compounds formed during the reaction again dissolve. After the addition of 8 g of diatomaceous earth and subsequently 115 cc of concentrated ammonia (approx. 27%) cooling is effected to about 30° while stirring and the resulting precipitate is filtered off. The filter residue is washed with 2–3 330 cc portions of toluene. The filtrate is subsequently mixed with water and the organic phase is extracted with dilute, approx. 10% hydrochloric acid. The base is precipitated by the dropwise addition of the hydrochloric acid extract to an excess of dilute ammonia. The precipitate is subsequently taken up in ether, the ether solution is washed with water and dried over sodium sulphate. After removing the ether by evaporation, the residue is dissolved in acetone and 38 g of maleic acid are added to the solution. The solution is subsequently concentrated, ethyl acetate and some ether are added and the resulting precipitate is filtered off. After recrystallization from acetone/ethyl acetate/ether, the resulting 6-(4-tert-butyl-1-piperazinyl)-morphantridine maleate has a M.P. of 138°–141°.

The 1-tert-butyl piperazine, used as starting material in the above process, may be produced as follows:

1. 1-benzyl-4-tert-butyl piperazine

A solution of 2000 g of bis-(2-chloroethyl)-tert-butylamine in 500 cc of ethanol and a solution of 1095 g of benzylamine in 750 cc of ethanol are simultaneously added dropwise to 1000 cc of boiling ethanol. After the addition is complete, the reaction mixture is heated to the boil for 1 hour. The mixture is subsequently concentrated in a vacuum and the residue is dissolved in dilute hydrochloric acid. The acid solution is washed with ether and is subsequently rendered alkaline with a concentrated, aqueous sodium hydroxide solution. The liberated base is extracted with ether and the ether residue is distilled. 1-benzyl-4-tert-butyl piperazine has a B.P. of 160°–162° at 12 mm of Hg.

2. 1-tert-butyl piperazine 348.5 g of 1-benzyl-4-tert-butyl piperazine are dissolved in 1200 cc of 99% ethanol and 10 g of a 5% palladium/charcoal catalyst are added to the resulting solution. The solution is subsequently shaken in a hydrogenation apparatus, in a hydrogen atmosphere (1 atmosphere) and at room temperature, until the take up of hydrogen is complete. Filtration is subsequently effected, the filtrate is concentrated by evaporation in a vacuum and the residue is distilled in a vacuum. 1-tert-butyl piperazine is obtained in the form of a colourless oil, having a B.P. of 66°–70° at 12 mm of Hg, which crystallizes upon standing. The crystals have a M.P. of 35°–40°.

By using the processes described in the above Examples 1 and 2 and the corresponding starting materials, the following compounds may be obtained in analogous manner:

5-methyl-11-(4-methyl-1-piperazinyl)-dibenzo[b,e][1,4]-diazepine, having a M.P. of 122°–124° (from ether/petroleum ether), 2-chloro-11-(4-methyl-1-piperazinyl)-dibenzo[b,f][1,4]-thiazepine, having a M.P. of 116°–120° (from ether/petroleum ether), 6-(4-methyl-1-piperazinyl)-merphantridine, having a M.P. of 138°–139° (from acetone/petroleum ether), 2-methyl-11-(4-methyl-1-piperazinyl)-dibenzo[b,f][1,4]-thiazepine, having a M.P. of 99°–107° (from petroleum ether), 2-chloro-11-(4-methyl-1-piperazinyl)-dibenz[b,f][1,4]-oxazepine, having a M.P. of 104°–110° (from petroleum ether), 2-bromo-11-(4-methyl-1-piperazinyl)-dibenzo[b,f][1,4]-thiazepine, having a M.P. of 138°–139° (from acetone/petroleum ether), 2-nitro-11-(4-methyl-1-piperazinyl)-dibenz[b,f][1,4]oxazepine, having a M.P. of 192°–193° (from chloroform/acetone/petroleum ether), 2-dimethylaminosulphonyl-11-(4-methyl-1-piperazinyl)-dibenzo[b,f][1,4]thiazepine, having a M.P. of 192-193° (from acetone/petroleum ether), 2-dimethylaminosulphonyl-11-(4-methyl-1-piperazinyl)-dibenz[b,f][1,4]oxazepine, having a M.P. of 149°–150° (from ether/petroleum ether), 2-methylsulphonyl-11-(4-methyl-1-piperazinyl)-dibenz[b,f][1,4]oxazepine, having a M.P. of 178°–179° (from acetone/ether/petroleum ether), 2-trifluoromethoxy-11-(4-methyl-1-piperazinyl)-dibenz[b,f][1,4]oxazepine dihydrochloride monohydrate, having a M.P. of 200-210° (from alcohol/ether), 7-chloro-4-(4-methyl-1-piperazinyl)-thieno[2,3-b][1,5]-benzothiazepine, having a M.P. of 162°–164° (from ethyl acetate), 2-trifluoromethylsulphonyl-11-(4-methyl-1-piperazinyl)-dibenzo[b,f][1,4thiazepine, having a M.P. of 168°–170° (from ether/petroleum ether), 2-acetyl-11-(4-methyl-1-piperazinyl)-dibenz[b,f][1,4]-oxazepine, having a M.P. of 116°–118° (from acetone/petroleum ether), 2-trifluoromethyl-11-(4-methyl-1-piperazinyl)-dibenz[b,f][1,4]oxazepine, the fumarate thereof having a M.P. of 214°–216° (from acetone/petroleum ether), 2-trifluoromethylsulphonyl-11-(4-methyl-1-piperazinyl)-dibenz[b,f][1,4]oxazepine, having a M.P. of 120°–122° (from ether/petroleum ether), 2-methylsulphonyl-11-(4-ethyl-1-piperazinyl)-dibenz[b,f][1,4]oxazepine, having a M.P. of 190°–191° (from acetone/petroleum ether), 4-(4-methyl-1-piperazinyl)-thieno[2,3-b][1,5]benzothiazepine, having a M.P. of 112°–114° (from absolute ethanol).

4-(4-methyl-1-piperazinyl)-10H-thieno[3,2-c][1]-benzazepine, having a M.P. of 145°–147° (from ether/petroleum ether), 8-chloro-4-(1-piperazinyl)-10H-thieno[3,2-c][1]-benzazepine, having a M.P. of 80°–100° (from acetone/water in the presence of charcoal), 8-chloro-4-[4-(2-acetoxyethyl)-1-piperazinyl]-10H-thieno[3,2-c][1]benzazepine, having a M.P. of 185°–189° (from ether/petroleum ether), 8-chloro-4-(4-methyl-1-piperazinyl)-10H-thieno-[3,2-c][1]benzazepine, having a M.P. of 193°–195° (from acetone/petroleum ether), 2-methylthio-11-(4-methyl-1-piperazinyl)-dibenz-[b,f][1,4]oxazepine, having a M.P. of 198°–201° (maleate), 4-(4-tert-butyl-1-piperazinyl)-10H-thieno[3,2-C][1]-benzazepine, having a M.P. of 147°–176° (maleate), 7-methyl-4-(4-methyl-1-piperazinyl)-10H-thieno-[3,2-c][1]benzazepine, having a M.P. of 180°–181° (from acetone/petroleum ether), 7-chloro-4-(4-methyl-1-piperazinyl)-10H-thieno-[3,2-c][1]benzazepine, having a M.P. of 184°–185° (from acetone), 7-chloro-4-(4-β-hydroxyethyl-1-piperazinyl)-10H-thieno[3,2-c][1]benzazepine, having a M.P. of 192°–194° (from ethyl acetate), 8-chloro-4-(4-β-hydroxyethyl-1-piperazinyl-10H-thieno[3,2-c][1]benzazepine, having a M.P. of 202°–203° (from ethyl acetate), 2-trifluoromethylsulphonyl-11-[4-(β-pentanoyloxyethyl)-1-piperazinyl]-dibenz[b,f][1,4]oxazepine, the oxalate thereof having a M.P. of 213°–216°, 2-trifluoromethylsulphonyl-11-(4-β-hydroxyethyl-1-piperazinyl)-dibenz[b,f][1,4]oxazepine, having a M.P. of 121°–123° (from ether/petroleum ether), 2-trifluoromethylsulphonyl-11-(1-piperazinyl)-dibenz[b,f][1,4]oxazepine, having a M.P. of 183-186° (from ether), 2-trifluoromethylsulphonyl-11-(4-β-hydroxypropyl-1-piperazinyl)-dibenz[b,f][1,4]oxazepine, having a M.P. of 132°–134° (from ether/petroleum ether), 2-trifluoromethylthio-11-(4-β-hydroxyethyl-1-piperazinyl)-dibenz[b,f][1,4]oxazepine, having a M.P. of 121°–123° (from petroleum ether), 2-trifluoromethylsulphonyl-11-(4-β-oleyloxyethyl-1-piperazinyl)dibenz[b,f][1,4]oxazepine (oil with an Rf value=0.88 [silicagel SL 254 Antec]to using chloroform/cyclohexane/diethyl amine (5:4:1) as eluant and Dragendorff's reagent as detection agent), 1,4-dimethyl-11-(4-methyl-1-piperazinyl)-dibenz-[b,f][1,4]oxazepine, having a M.P. of 143°–144° (from ether/petroleum ether), 3,4-dimethyl-11-(4-methyl-1-piperazinyl)-dibenz-[b,f][1,4]oxazepine, having a M.P. of 167°–169° (from acetone/petroleum ether), 2,8-dichloro-11-(4-methyl-1-piperazinyl)-dibenz-[b,f][1,4]oxazepine, having a M.P. of 130°–131° (from acetone/petroleum ether), 4,8-dichloro-11-(4-methyl-1-piperazinyl)-dibenz-[b,f][1,4]oxazepine, having a M.P. of 134°–135° (from acetone/petroleum ether), 4-methyl-8-chloro-11-(4-methyl-1-piperazinyl)-dibenz-[b,f][1,4]oxazepine, having a M.P. of 150°–151° (from ether/petroleum ether), 4-methyl-7-chloro-11-(4-methyl-1-piperazinyl)-dibenz-[b,f][1,4]oxazepine, having a M.P. of 167°–168° (from acetone/petroleum ether), 2,4-dichloro-11-(4-methyl-1-piperazinyl)-dibenz-[b,f][1,4]oxazepine, having a M.P. of 135°–138° (from acetone/petroleum ether), 2-chloro-11-(1-piperazinyl)-debenz[b,f][1,4]oxazepine, having a M.P. of 178°–180° (from acetone/petroleum ether).

The starting materials for the production of 10H-thieno[3,2-c][1]benzazepines may be obtained as follows:

4,5-dihydro-10H-thieno[3,2-c][1]benzazepin-4-one 14.8 g of 2-(2-amino-phenyl)-thienone, 23.8 g of solid potassium hydroxide and 19.6 g of hydrazine hydrate are heated to the boil at reflux in 180 cc of diethylene glycol for 3 hours. After diluting the reaction mixture with ice water, extraction is effected with ether. The ether phase is washed thrice with water, dried over sodium sulphate and concentrated. 2-(2-aminobenzyl)-thiophene is obtained in the form of a light yellow oil having a B.P. of 128°–130° at 0.1 mm of Hg.

46 cc of a 20% solution of phosgene in toluene are added dropwise at −3°, with stirring, to a solution of 9.8 g of the product obtained above in 60 cc of toluene. The reaction mixture is subsequently allowed to warm to room temperature while passing through a stream of phosgene, and is then heated to the boil at reflux for half an hour. After driving out the excess phosgene with a stream of nitrogen, the reaction mixture is concentrated in a vacuum and the residue is distilled. 10.8 g of 2-(2-isocyanato-benzyl)-thiophene, having a B.P. of 108° at 0.05 mm of Hg, are obtained.

10.5 g of 2-(2-isocyanato-benzyl)-thiophene (B.P. 108°/0.05 mm of Hg) are heated to 110° with 105 g of polyphosphoric acid for 1 hour while stirring. The reaction mixture is subsequently rendered alkaline with a concentrated ammonia solution while cooling internally and externally with ice and the resulting precipitate is filtered off. This is washed with water, dried and crystallized from acetone while treating with charcoal. 4,5-dihydro-10H-thieno[3,2-c][1]benzazepin-4-one is obtained in the form of grains having a M.P. of 225°–236° (between 150° and 200° conversion into bright needles).

8-chloro- or
7-chloro-4,5-dihydro-10H-thieno[3,2-c][1]benzazepin-4-one 6 g of N-p-toluenesulphonyl-5-chloro or 4-chloro)-anthranilic acid are heated to the boil at reflux with 10 cc of thionyl chloride for 1½ hours. After evaporating to dryness in a vacuum, the residue is recrystallized from methylene chloride/petroleum ether. The resulting N-p-toluenesulphonyl-5-chloro-anthranilic acid chloride has a M.P. of 134°–136°, N-p-toluenesulphonyl-4-chloro-anthranilic acid chloride has a M.P. of 135°–140°.

A solution of 6 g of stannic chloride in 10 cc of carbon disulphide is slowly added dropwise at the boil, under reflux, to a mixture of 7 g of finely pulverized N-p-toluenesulphonyl-5-chloro (or 4-chloro)-anthranilic acid chloride and 3.4 g of thiophene in 25 cc of carbon disulphide. After the addition is complete, stirring is effected at room temperature for 2 hours. The solvent is subsequently evaporated in a vacuum, the residue is treated with ice water and hydrochloric acid and extracted with ethyl acetate. The ethyl acetate extract is washed with 2N hydrochloric acid, water and a saturated aqueous potassium bicarbonate solution, is dried with sodium sulphate and concentrated. The evaporation residue is divided between ether and a 1 normal aqueous sodium hydroxide solution. The aqueous alkaline solution is acidified with concentrated hydrochloric acid and the resulting precipitate is drawn off by suction. The suction filter residue is washed with water and recrystallized from ethyl acetate/petroleum ether. 2-(2-p-toluenesulphonamido-5-chloro-phenyl)-thienone has a M.P. of 164°–167°, 2-(2-p-toluenesulphonamide-4 -chloro-phenyl)-thienone has a M.P. of 140°–141°.

8.4 g of 2-(2-p-toluenesulphonamido-5-chloro (or 4-chloro)-phenyl)-thienone are stirred at room temperature with 100 cc of concentrated sulphuric acid for 4 hours. The reaction product is subsequently poured on ice and the resulting mixture is rendered alkaline with a concentrated aqueous sodium hydroxide solution while cooling. A precipitate is obtained, which is taken up in ether. The ether solution is washed with water, dried with sodium sulphate and concentrated, whereby a residue is obtained. After recrystallization from ether/petroleum ether in the presence of charcoal and aluminium oxide, 2-(2-amino-5-chloro-phenyl)-thienone has a M.P. of 97°–98° and 2-(2-amino-4-chloro-phenyl)-thienone has a M.P. of 66°–72°.

15.5 g of 2-(2-amino-5-chloro (or 4-chloro)-phenyl)-thienone, 23.8 g of solid potassium hydroxide and 19.6 g of hydrazine hydrate are heated to the boil at reflux in 180 cc of diethylene glycol for 2 hours. After diluting the reaction mixture with ice water, extraction is effected with ether. The ether phase is washed thrice with water, dried with sodium sulphate and concentrated. 2-(2-amino-5-chloro-benzyl)-thiophene, having a B.P. of 150°–157° at 0.1 mm of Hg, and 2-(2-amino-4-chloro-benzyl)-thiophene, having a B.P. of 137°–140° at 0.05 mm of Hg, are obtained in the form of an oil.

46 cc of a 20% solution of phosgene in toluene are added dropwise at −3°, while stirring, to a solution of 11 g of 2-(2-amino-5-chloro (or 4-chloro)-benzyl)-thiophene in 60 cc of toluene. The reaction mixture is subsequently allowed to warm to room temperature while introducing a stream of phosgene and is subsequently heated to the boil at reflux for half an hour. After driving off the excess phosgene with a nitrogen stream, the reaction mixture is concentrated in a vacuum and the residue is distilled. 2-(2-isocyanato-5-chloro-benzyl)-thiophene, having a B.P. of 137°–139° at 0.1 mm of Hg, and 2-(2-isocyanato-4-chloro-benzyl)-thiophene, having a B.P. of 124°–125° at 0.05 mm of Hg, are obtained.

Ring closure of 2-(2-isocyanato-5-chloro (or 4-chloro)-benzyl)-thiophene, using the process described above with respect to 2-(2-isocyanatobenzyl)thiophene, yields 8-chloro-4,5-dihydro-10H-thieno[3,2-c][1]benzazepin-4-one, having a M.P. of 280°–281° (after recrystallization from dioxane/acetone), and 7-chloro-4,5-dihydro-10H-thieno[3,2-c][1]benzazepin-4-one, having a M.P. of 264°–266° (after recrystallization from acetone).

Following the procedure described in Example 1 or 2 but replacing the starting materials with appropriate compounds in equivalent amounts, the following compounds are prepared:

2-methoxy-11-(4-methyl-1-piperazinyl)dibenz [b,f][1,4]-oxazepine; 2-fluoro-11-(4-methyl-1-piperazinyl)dibenz-[b,f][1,4]oxazepine;

2-cyano-11-(4-methyl-1-piperazinyl)dibenz-[b,f][1,4]oxazepine;

2,4-difluoro-11-(4methyl-1-piperazinyl)dibenz-[b,f][1,4]oxazepine; 2,4-dibromo-11-(4-methyl-1-piperazinyl)dibenz-[b,f][1,4]oxazepine;

8-methoxy-11-(4-methyl-1-piperazinyl)dibenzo-[b,f][1,4]thiazepine;

7-methylthio-11-(4-methyl-1-piperazinyl)dibenzo-[b,f][1,4]thiazepine;

8-fluoro-11-(4-methyl-1-piperazinyl)dibenz-[b,f][1,4]oxazepine;

8-bromo-11-(4-methyl-1-piperazinyl)dibenz-[b,f][1,4]oxazepine;

8-trifluoromethyl-11-(4-methyl-1-piperazinyl)-5H-dibenzo[b,e][1,4]diazepine; and 2-nitro-11-(4β-methoxyethyl-1-piperazinyl)dibenz-[b,f][1,4]oxazepine.

What is claimed is:

1. A process for the production of a compound of formula I,

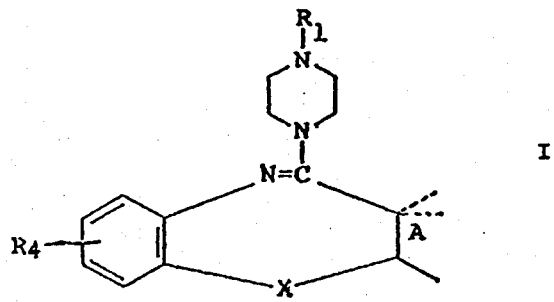

wherein
- $R_1$ is hydrogen, alkoxyalkyl of 2 to 6 carbon atoms in the aggregate thereof, alkyl of 1 to 4 carbon atoms, hydroxyalkyl of 1 to 4 carbon atoms, or alkanoyloxalkyl of 3 to 22 carbon atoms in the aggregate thereof,
- $R_4$ is hydrogen, alkyl, alkoxy or alkylthio, wherein the alkyl groups have 1 to 4 carbon atoms, halogen, or trifluoromethyl, and
- a. A is

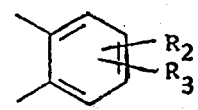

wherein $R_2$ is hydrogen, alkyl, dialkylaminosulphonyl, alkylsulphonyl, wherein the alkyl groups have 1 to 4 carbon atoms, alkoxy or alkylthio of 1 to 4 carbon atoms, halogen, nitro, trifluoromethylsulphonyl, trifluoromethoxy, trifluoromethylthio, acetyl, cyano or trifluoromethyl, and $R_3$ is hydrogen, halogen or alkyl of 1 to 4 carbon atoms, and X is $-CH_2-$, $-O-$, $-S-$, $-\overset{|}{N}H$ or $-\overset{|}{N}$-alkyl wherein the alkyl group has 1 to 3 carbon atoms, or b. A is

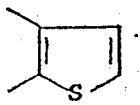

and X is $-CH_2-$ or $-S-$, which comprises reacting a compound of formula II,

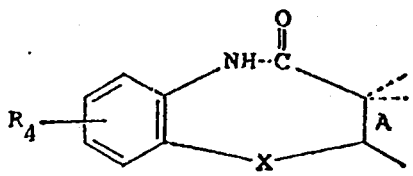

wherein X, A and $R_4$ are as defined above, with a metal-amine complex wherein the metal is titanium, zirconium, hafnium or vanadium, and the amine is a compound of formula III,

wherein $R_1$ is as defined above.

2. A process according to claim 1, in which the metal-amine complex is formed by reacting a tetrachloride or tetrabromide of the metal with a compound of formula III.

3. A process according to claim 2, in which the mol ratio of metal tetrachloride or tetrabromide to compound of formula III is about 1:4.

4. A process according to claim 1, carried out in the presence of a tertiary amine as an acid-binding agent, the mol ratio of the tertiary amine to metal-amine complex being at least 2:1.

5. A process according to claim 1, wherein $R_1$ is hydroxyalkyl of 1 to 4 carbon atoms, and the reaction is carried out in the presence of a large amount of solvent in the presence of at least a ten fold excess of a tertiary amine over the metal-amine complex.

6. A process according to claim 1, carried out in the presence of chlorobenzene, toluene or anisole, as solvent.

7. A process according to claim 1, carried out at a temperature form 20° to 150°C.

8. A process according to claim 1, wherein $R_3$ is hydrogen.

* * * * *

UNITED STATES PATENT AND TRADEMARK OFFICE

CERTIFICATE EXTENDING PATENT TERM
UNDER 35 U.S.C. 156

Patent No.    : 3,962,248

Dated         : June 8, 1976

Inventor(s)   : Josef Schneider

Patent Owner  : Sandoz Pharmaceuticals Corporation

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

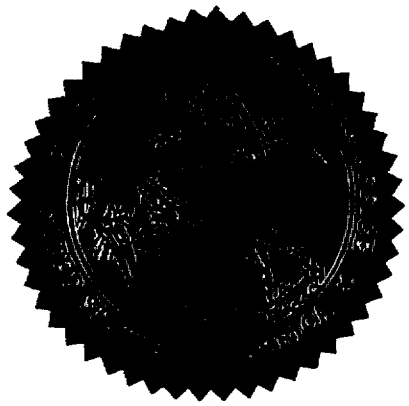

I have caused the seal of the Patent and Trademark Office to be affixed this 26th day of November 1990.

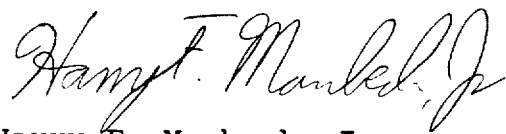

Harry F. Manbeck, Jr.
Assistant Secretary and Commissioner
of Patents and Trademarks